US007770827B2

(12) United States Patent
Lukashevych et al.

(10) Patent No.: US 7,770,827 B2
(45) Date of Patent: Aug. 10, 2010

(54) CEREAL GRAIN TREATMENT AND MASH PREPARATION FOR BY-PRODUCTS

(75) Inventors: Yevgen Lukashevych, Kyiv (UA); Artem Dyba, Kyiv (UA)

(73) Assignee: Ukrainian Technological Company, Kyiv (UA)

( * ) Notice: Subject to any disclaimer, the term of this patent is extended or adjusted under 35 U.S.C. 154(b) by 364 days.

(21) Appl. No.: 11/947,416

(22) Filed: Nov. 29, 2007

(65) Prior Publication Data

US 2009/0142448 A1 Jun. 4, 2009

(51) Int. Cl.
*B02C 9/00* (2006.01)
(52) U.S. Cl. .............................................. 241/7; 241/11
(58) Field of Classification Search ................. 241/6–7, 241/9, 11, 13
See application file for complete search history.

(56) References Cited

U.S. PATENT DOCUMENTS

| 3,443,958 | A |   | 5/1969  | Dennis et al.        |       |
|-----------|---|---|---------|----------------------|-------|
| 4,448,881 | A |   | 5/1984  | Muller et al.        |       |
| 4,810,647 | A |   | 3/1989  | Monceaux et al.      |       |
| 5,024,148 | A |   | 6/1991  | Moses                |       |
| 5,115,984 | A | * | 5/1992  | Satake ............   | 241/7 |
| 5,209,158 | A |   | 5/1993  | Salete               |       |
| 5,295,629 | A |   | 3/1994  | Satake et al.        |       |
| 5,511,469 | A |   | 4/1996  | Satake et al.        |       |
| 5,516,048 | A | * | 5/1996  | Falk ..............   | 241/7 |
| 5,678,477 | A |   | 10/1997 | Satake et al.        |       |
| 5,820,039 | A |   | 10/1998 | Martin et al.        |       |
| 7,101,691 | B2 |  | 9/2006  | Kinley et al.        |       |
| 7,138,257 | B2 |  | 11/2006 | Galli et al.         |       |
| 7,141,260 | B2 |  | 11/2006 | Cope et al.          |       |
| 2004/0023349 | A1 | | 2/2004 | Bisgaard-Frantzen et al. | |
| 2004/0234649 | A1 | | 11/2004 | Lewis et al. | |
| 2005/0025868 | A1 | | 2/2005 | Karl et al. | |
| 2005/0118692 | A1 | | 6/2005 | Kinley et al. | |
| 2005/0118693 | A1 | | 6/2005 | Thorre | |
| 2005/0233030 | A1 | | 10/2005 | Lewis et al. | |
| 2005/0239181 | A1 | | 10/2005 | Lewis et al. | |
| 2005/0266539 | A1 | | 12/2005 | Hochberg et al. | |
| 2006/0035354 | A1 | | 2/2006 | Galli et al. | |
| 2006/0194296 | A1 | | 8/2006 | Hammond et al. | |
| 2006/0251764 | A1 | | 11/2006 | Abbas et al. | |

(Continued)

FOREIGN PATENT DOCUMENTS

GB 2268386 A 1/1994

*Primary Examiner*—Faye Francis
(74) *Attorney, Agent, or Firm*—Price, Heneveld, Cooper, DeWitt & Litton, LLP

(57) ABSTRACT

An apparatus and method for dry treatment of grain comprises a grain peeler for mechanically treating pre-cleaned grain to remove flour bran and coarse bran to a peeling depth of about 4% to 9% with simultaneous separating of the flour bran; an aspiration separator separating coarse bran based on particle velocity and size; a grain mill; and sieve separator separating the husk bran of between 2%-3% of the grain kernel mass from endosperm flour by differences in particle size. An apparatus and method for mash preparation from the endosperm flour comprises mixing tank for mixing endosperm flour with water, enzymes, etc; a colloid mill for processing the batch using mechano-activation with oscillation frequencies between 1 and 200 kHz and with impulse duration of between 0.05 and 1.0 seconds and for 2 to 20 processing cycles, coarse particle sifter for separation of the coarse batch particles form the mash.

6 Claims, 4 Drawing Sheets

U.S. PATENT DOCUMENTS

2006/0286654 A1 12/2006 Kinley et al.
2007/0037267 A1 2/2007 Lewis et al.
2007/0099278 A1 5/2007 Aare
2007/0184541 A1 8/2007 Karl et al.

* cited by examiner

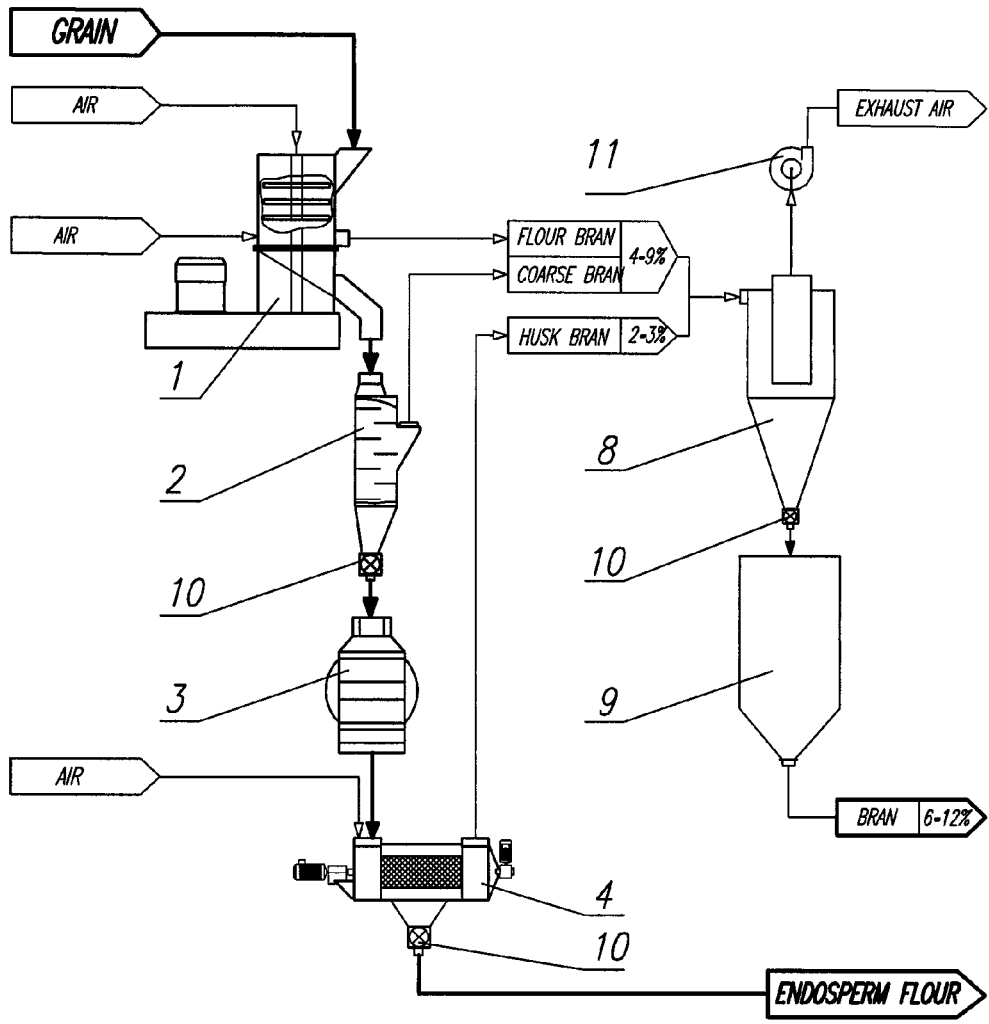
Fig.1 Schematic view illustrating an arrangement of equipment of the dry cereal grain treatment:
*1-Grain peeler; 2-Aspiration separator; 3-Grain mill; 4-Sieve separator; 8-Cyclone; 9-Storage silo; 10-Back valve; 11-Blower.*

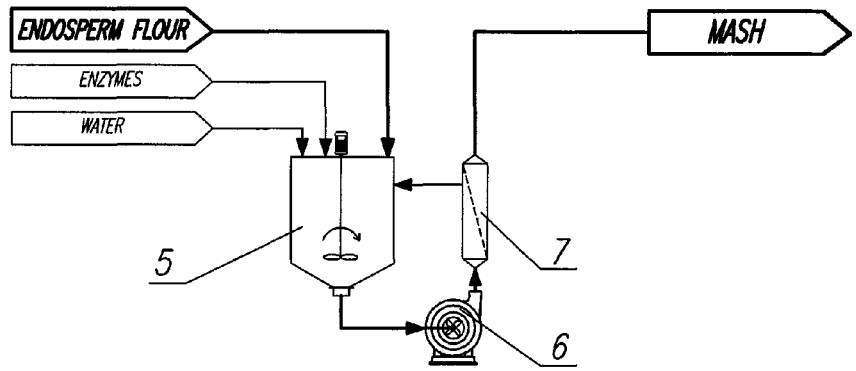

Fig.2 Schematic view illustrating an arrangement of equipment of the mash preparation from the endosperm flour:

*5-Mixing tank; 6-Colloid mill; 7-Coarse particle sifter.*

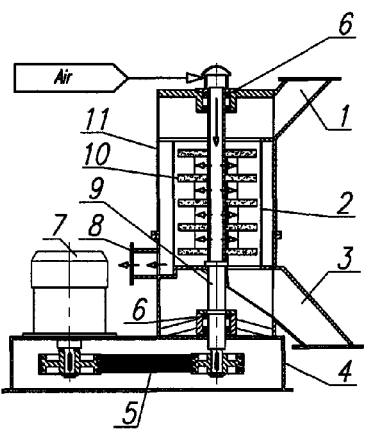

Fig.3 Cross-section of grain peeler:

*1-Inlet nozzle; 2-Sifting cylinder; 3-Outlet nozzle; 4-Ancor base; 5-V-belt drive; 6-Bearing support; 7-Electric motor; 8-Outlet nozzle husk; 9-Shaft; 10-Abrasive disk; 11-Case of working chamber.*

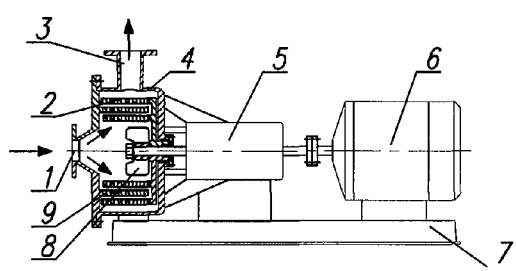

Fig.4 Cross-section of colloid mill:

*1-Inlet nozzle; 2-Rotor; 3-Outlet nozzle; 4-Case of working chamber; 5-Bearing unit; 6-Electric motor; 7-Ancor base; 8-Impeller; 9-Stator.*

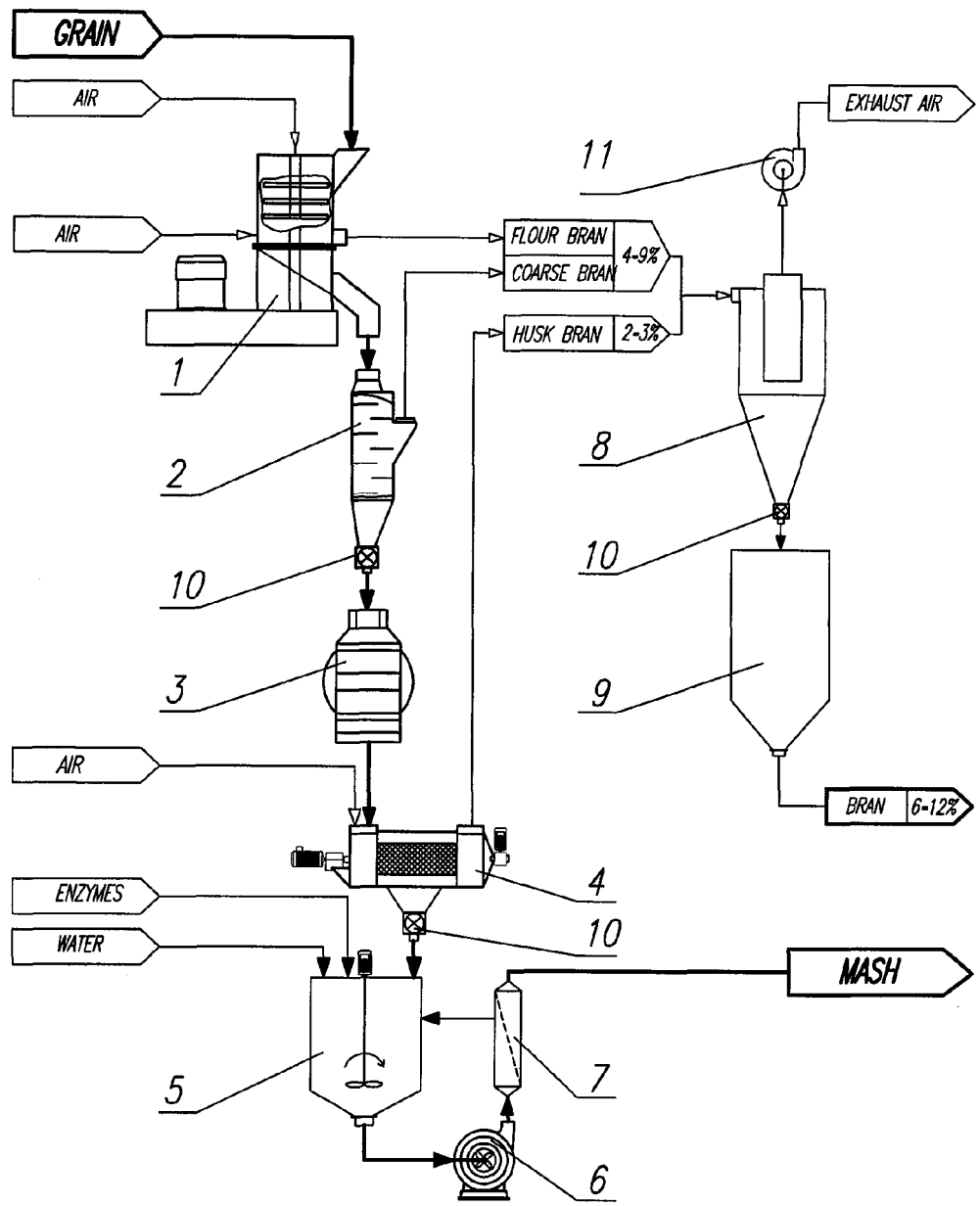
Fig.5  Schematic view illustrating an arrangement of equipment of the combined process for dry cereal grain treatment and mash preparation:
1-Grain peeler; 2-Aspiration separator; 3-Grain mill; 4-Sieve separator; 5-Mixing tank; 6-Colloid mill; 7-Coarse particle sifter; 8-Cyclone; 9-Storage silo; 10-Back valve; 11-Blower.

Flow sheet of the process of cereal grain treatment and mash preparation

CEREAL GRAIN TREATMENT AND MASH PREPARATION FOR BY-PRODUCTS

BACKGROUND

The present invention relates to cereal grain treatment for efficiently obtaining by-products of the grain. More particularly, the present invention relates to methods of cereal grain preparation that eliminate water and chemicals to prepare milling (in this case endosperm flour) for production of ethyl alcohol, bioethanol, starch, glucose-fructose syrup, and other products of grain hydrolysis. Further, the present invention relates to subsequent methods of mash preparation including water and using mechano-activation.

Known prior art technology requires the use of water in the process of removing outer layers of grain. The water addition requires the peeling process to include additional stages such as initial wetting and tempering of the grain. Specifically, current practices of removal of outer layers from grain kernels (called "peeling"), involve either grain soaking in water, or treating the grain with chemicals (such as strong bases) along with the subsequent peeling of outer layers via mechanical treatment. These current practices have major drawbacks, such as large volumes of water and chemicals used in the process, the use of a number of complicated operations requiring costly equipment, and high wheat quality demands. By high wheat quality demands, it is meant that broken grain has to be separated before the peeling process. This makes current methods unsuitable for alcohol and bioethanol industries, since these industries use fodder (feeder) wheat. Furthermore, the above mentioned peeling methods increase grain moisture content by 20% to 30%, whereas grain moisture content higher than 12% to 15% hampers the milling of grain kernels in the grain mill.

Another problem is found as the mash is further processed in a practice known as mechano-activation. Specifically, milled non-peeled starch-containing raw material (wheat) causes poor performance of the mechano-activation process by causing premature failure of mechano-activation equipment, due to coarse and abrasive particles such as sand and other impurities present on the surface of the grain. The resulting problems with mechano-activation equipment may consist of regular equipment clogging up and premature deterioration (excessive wear) of the rotating cylinders, which are the core elements of the mechano-activation equipment. Specifically, the drawbacks of known methods causing premature failure of the mechano-activation equipment are due in part to the abrasive and coarse particles present in the mixture, and also are due to the low efficiency of the mechano-activation process due to insufficient starch solubilization and low enzyme activation levels.

SUMMARY OF THE PRESENT INVENTION

In one aspect of the present invention, a process of dry cereal grain treatment for ethanol, bioethanol, starch and syrup industries comprises the steps of providing past harvest grain stock; mechanically treating the surface of the unmilled grain to remove coarse bran and flour bran from remaining grain product; separating of the coarse bran and flour bran from the remaining grain product; milling the remaining grain product to form a milled grain product; and separating the husk bran from the milled grain product. In a narrower aspect, no water is added during the process. In a preferred form, the final product is an endosperm flour.

In another aspect of the present invention, a method of mash preparation for ethanol, bioethanol, starch and syrup industries includes steps of providing endosperm flour, mixing the endosperm flour with water to form a batch, processing the batch using mechano-activation to reduce particle size of the endosperm flour, and sieving the batch to remove coarse batch particles from the batch to leave a desired final mash product.

In still another aspect of the present invention, a grain peeler for cereal grains outer layers removal, includes a set of horizontally oriented abrasive discs allocated on one shaft in an abrasion chamber; a cylindrical working chamber located just below the set of abrasive discs and having a sieve formed by perforated sidewalls; and a pressure fan joined to the working chamber.

In still another aspect of the present invention, a cavitation mechano-activation apparatus includes a cylindrical chamber having an axled inlet nozzle and radial outlet nozzle; a stator including at least one stationary perforated pipe section adjoined to a back wall of the cylindrical chamber; and a rotor including an impeller and at least two moving perforated pipe sections adjoined to a round backplane and which are fixed to a shaft of the rotor, the at least two moving perforated pipe sections overlapping the stationary perforated pipe section.

In still another aspect of the present invention, an apparatus for treatment of grain stock comprises a grain peeler for receiving the past harvest grain stock. The grain peeler subjects the grain stock to mechanical surface treatment by one or both of friction and abrasion to remove flour bran and coarse bran with the peeling depth from about 4% to 9% of a mass of the grain kernel; and simultaneously, the grain peeler separates flour bran from the grain stock by particle size differences. The apparatus further includes an aspiration separator for receiving the grain stock from the grain peeler in order to separate coarse bran from the grain stock, the aspiration separator functioning based on difference in particle velocity and size. A grain mill is provided for receiving the grain stock from the aspiration separator, the grain mill being configured to mill the grain stock. A sieve separator is configured to receive the grain stock from the grain mill, the grain stock including grain kernel mass that is husk bran and endosperm flour; the sieve separator being configured to separate the husk bran in an amount of about 2%-3% of the grain kernel mass from endosperm flour by differences in particle size.

In still another aspect of the present invention, an apparatus for mash preparation for ethanol, bioethanol, starch and syrup industries comprises a mixing tank for mixing endosperm flour with water, a colloid mill for processing the batch using mechanoactivation, and a coarse particle sifter for separating the batch coarse particles from the mash.

In still another aspect of the present invention, a method for treatment of grain stock, comprises steps of providing the post harvest cleaned grain stock; subjecting the grain stock to mechanical surface treatment by one or both of friction and abrasion to remove flour bran and coarse bran with the peeling depth from about 4% to 9% of a mass of the grain kernel; simultaneously, separating flour bran from the grain stock by particle size differences. The method further includes separating coarse bran from the grain stock based on difference in particle velocity and size; milling the grain stock, the grain stock having grain kernel mass including husk bran and endosperm flour; and separating the husk bran in an amount of about 2%-3% of the grain kernel mass from the endosperm flour by differences in particle size.

In still another aspect of the present invention, a method for mash preparation for ethanol, bioethanol, starch and syrup industries comprises steps of mixing the endosperm flour with water, subjecting the batch to a mechano-activation process in a range of oscillation frequencies between 1 and 200 kHz, with impulse duration of 0.05 to 1.0 seconds and for 1 to 20 processing cycles to form a mash, and separating batch coarse particles from the mash.

In yet another aspect of the present invention, a method for treatment of grain stock, comprises steps of treating dry grain stock with dry mechanical surface treatment, including separating flour bran from coarse bran and thereafter milling the peeled grain and separating the husk bran from the endosperm flour.

An object of the present invention is to eliminate the use of water and chemicals during the removal of outer layers from grain. The grain outer layers are removed in a dry environment, without addition of water.

An object of the present invention is to eliminate changes to grain moisture content during grain preparation.

An object of the present invention is to eliminate application of fine impurities grain separator in the process of grain treatment.

An object of the present invention is to apply the peeling machine instead of fine impurities grain separator in the process of grain treatment.

An object of the present invention is to reduce energy consumption when milling grain, as well as reducing wear and tear on milling equipment used during the milling process.

An object of the present invention is to allow use of "lower-purity" grades of wheat while still meeting the quality demands of "higher-purity" grades of wheat.

In still another aspect of the present invention, a method includes peeling of grain used as raw material to a depth of between 4% and 9% of a grain kernel mass, and thereafter milling the peeled grain, separating the husk bran in amount of 2-3% of an initial grain kernel mass, mixing with water in batch, and subjecting the batch to mechano-activation to prepare a mash suitable for production of ethyl alcohol, bioethanol, starch, glucose-fructose syrup, and other products of grain hydrolysis.

An object of the present invention is to raise an efficiency of the mechano-activation process through the improvement of starch solubilization and the increase in enzyme activation levels.

An object of the present invention is to reduce intensive wearing out of mechano-activation equipment and prevent equipment failure due to the presence of abrasive and coarse particles in the mixture. The invention increases starch solubilization and enzyme activation levels, thus increasing efficiency of the mechano-activation process.

An object of the present invention is to provide a mechano-activation process with a grain milling originated out of peeled grain with an outer layers removal and separation between 6% and 12% of the initial grain kernel mass including flour bran, coarse bran and husk bran.

These and other aspects, objects, and features of the present invention will be understood and appreciated by those skilled in the art upon studying the following specification, claims, and appended drawings.

BRIEF DESCRIPTION OF DRAWINGS

FIG. 1 is a schematic view illustrating an arrangement of equipment of the present process, the arrangement also representing a related method, where the process is a dry process for grain treatment without adding water to obtain grain product with a high percentage content of endosperm (i.e. endosperm flour).

FIG. 2 is a schematic view illustrating an arrangement of equipment of the present process, the arrangement also representing a related method, where the process is a process of the mash preparation from the endosperm flour using a mechano-activation process.

FIG. 3 is an enlarged schematic view of the grain peeler of FIG. 2.

FIG. 4 is an enlarged side view of the colloid mill of FIG. 3.

FIG. 5 is a schematic view illustrating an arrangement of equipment of the combined process for dry cereal grain treatment and mash preparation.

DETAILED DESCRIPTION OF PREFERRED EMBODIMENTS

Figure 6:
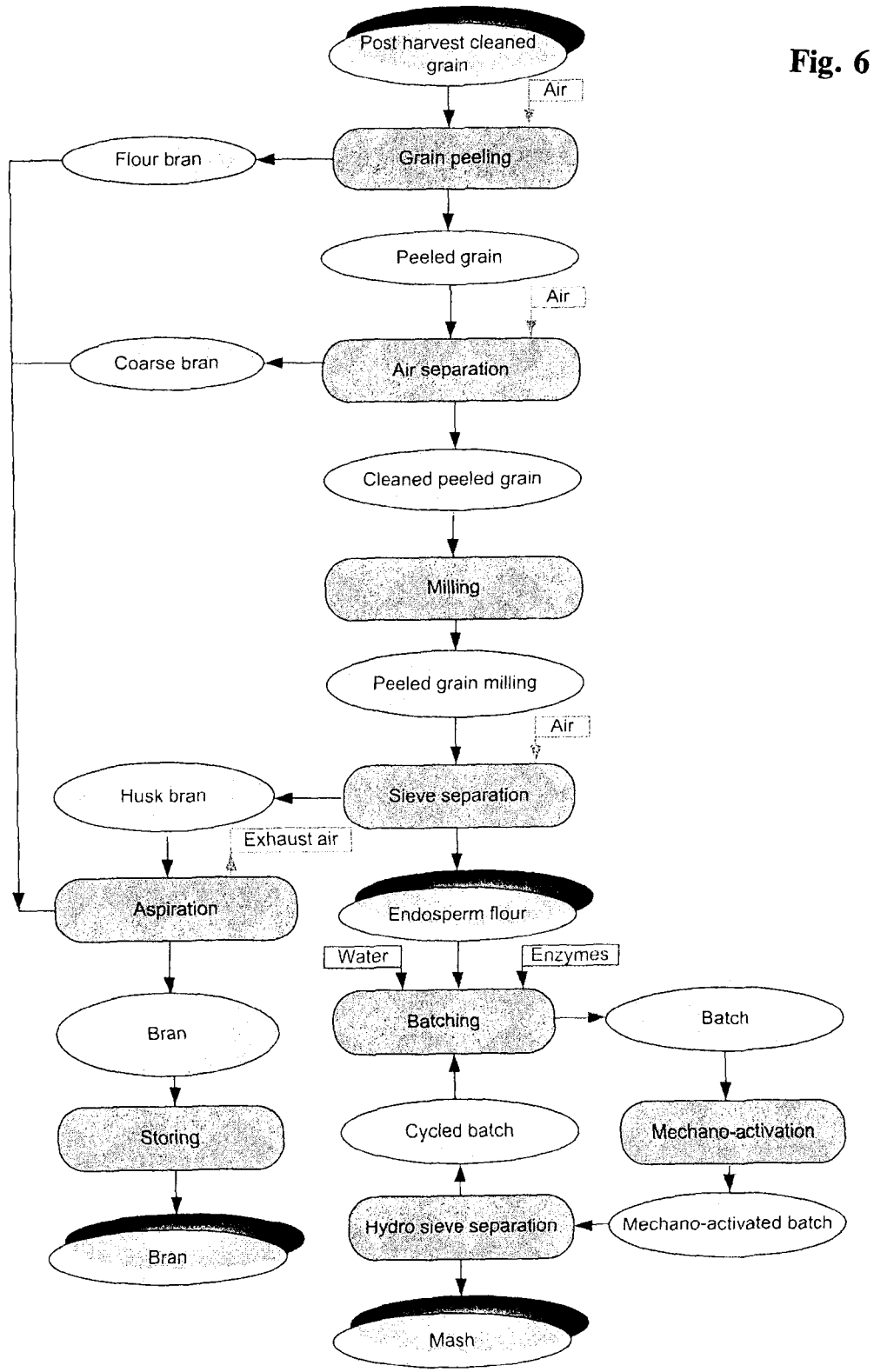
FIG. 6 is a flow chart showing a combined process of cereal grain treatment and mash preparation.

The following terms as used in reference to FIG. 1 are defined as used herein, and will be understood by persons having ordinary skill in this art upon reading the present disclosure. "Grain peeler" is a device that provides mechanical surface treatment of the grain by friction or abrasion or a combination thereof. The purpose of the grain peeler is to remove flour bran and coarse bran from grain kernel with simultaneous flour bran separation from the grain by particle size differences. "Aspiration separator" is a device that provides separation of the coarse bran from the peeled grain. The separation in the aspiration separator is achieved based on difference in particle velocity and size. "Grain mill" is a device that provides milling of the peeled grain to the endosperm flour and husk bran. "Sieve separator" is a device that provides separation of husk bran from endosperm flour by difference in particle size. "Mixing tank" is a vessel that provides mixing of the endosperm flour with water and enzymes, and further that provides homogenization of the batch. "Colloid mill" is a device that provides mechano-activation treatment, the processing with impulses of the fixed oscillation frequencies of the batch. "Coarse particle sifter" is a device that provides coarse batch particles separation from the mash.

Further, the following grain and product terms are used: "Post harvest cleaned grain stock" is grain stock from which coarse impurities (e.g., straw, big stones and metal particles) are separated. "Bran" is grain kernel component represented with its outer layers. "Bran flour" is bran fraction having a particle size smaller than 1 mm. "Coarse bran" is bran fraction having particles with sizes bigger than 1 mm. "Husk bran" is bran fraction having not particulate structure but film structure. "Endosperm flour" is remaining grain product in powder after removal and separation of bran from the initial grain. "Batch" is a multicomponent mixture that includes primarily endosperm flour, water, and enzymes. "Mash" is batch after processes of homogenization, mechano-activation, and coarse particles separation.

Initially, the pre-cleaned grain stock is fed to the grain peeler (1) in which it is subjected to mechanical surface treatment by friction or abrasion or a combination thereof, to remove flour bran and coarse bran with the peeling depth from 4% to 9% of the grain kernel mass. Simultaneously, flour bran is separated from the grain in the grain peeler (1) by particle size differences.

Thereafter, the stock is passed through the aspiration separator (2) in order to separate coarse bran from the grain. The separation in the aspiration separator is achieved based on difference in particle velocity and size.

After the separation, the grain stock is passed to the grain mill (3) for milling. Thereafter, the stock is passed to the sieve separator (4) in order to separate husk bran in amount of 2%-3% of the grain kernel mass from endosperm flour by differences in particle size. The outer layers, which are removed during the separation stages, are collected as byproduct for further processing and use. As evident from the above description, the proposed method requires no water. It is noted that the grain peeler separation chamber may clog and require periodic cleaning of the chamber for stable operation.

The following terms are used in reference to FIGS. 1, 2 and 5, and will be understood by persons having ordinary skill in this art upon reading the present disclosure. The apparatus includes: 1—grain peeler, 2—aspiration separator, 3—grain mill, 4—sieve separator; 5—hydrostatic mixer, 6—colloid mill (mechano-activation mill), 7—coarse particle sifter, 8—cyclone, 9—storage silo, 10—back valve, and 11—blower. Specifically, FIG. 1 illustrates an arrangement of equipment (items 1, 2, 10, 3, 4, 8, 10, and 9) for the dry cereal grain treatment, FIG. 2 illustrates an arrangement of equipment (items 5, 6, 7) for mash preparation from the endosperm flour, and FIG. 5 illustrates a combination of the illustrated processes of FIGS. 1 and 2.

The details of the grain peeler from FIG. 1 are shown in FIG. 3. The grain peeler (FIG. 3) includes: 1—inlet nozzle, 2—sifting cylinder, 3—outlet nozzle, 4—anchor base (engine bed), 5—V-belt drive, 6—bearing support, 7—electric motor, 8—outlet nozzle for husk, 9—shaft, 10—abrasive disk, and 11—case of working chamber.

The details of the colloid mill from FIG. 1 are shown in FIG. 4. The colloid mill apparatus (FIG. 4) includes: 1—inlet nozzle; 2—rotor, 3—outlet nozzle, 4—case of working chamber, 5—bearing unit, 6—electric motor, 7—anchor base, 8—impeller, 9—stator.

The details of the combined method are illustrated in FIG. 6. Post harvest cleaned grain is provided prior to a grain peeling step. Flour bran is separated and sent to an aspiration step. The peeled grain from the grain peeling step is sent to an air separation step where coarse bran is separated and sent to the aspiration step. Cleaned peeled grain from the air separation step is sent to a milling step. Peeled grain milling from the milling step is sent to a sieve separation step where husk bran is separated and sent to the aspiration step. The combined bran (flour bran, coarse bran, husk bran) is sent to a storing step and saved as a product for later use. Endosperm flour exits the sieve separation step and is combined with water and enzymes and mixed in a batching step. The batch created is treated in a mechano-activation component to create a mechano-activated batch. The mechano-activated batch is sent to a hydro sieve separation step, wherein one suitably-finished component (mash) is separated for use and also a second partially-treated component (cycled batch) is sent back to the matching step for continued recycling and treatment.

The present method includes peeling of pre-cleaned post-harvest grain used as raw material to a depth of between 4%-9% of a grain kernel mass, in order to achieve a peeled grain from which a high level of endosperm flour product can be made, but without use of water in the peeling process to obtain the peeled grain. Thereafter, the method includes subjecting the peeled grain to milling. Husk bran is separated at a level of about 2%-3% of the grain kernel mass. The batch is then subjected to mechano-activation to prepare a mash suitable for production of ethyl alcohol, bioethanol, starch, glucose-fructose syrup, and other products of grain hydrolysis.

According to a second part of the present method, endosperm flour is mixed with water in the mixing tank (5). Liquefying enzymatic agents are added to the batch, and the batch undergoes mechano-activation in the range of oscillation frequencies between 1 and 200 kHz, with impulse duration between 0.05 and 1.0 seconds. Then the batch is split into two flows: the first flow being recycled to the mixing tank (5) and the second flow (often called "batch permeate") permeating through the coarse particle sifter (7). The quantity of the batch processing cycles in the circuit of: mixing tank (5), colloid mill (6), and coarse particle sifter (7) is between 2 and 20 times (i.e., processing "cycles"). The batch permeate flowing through the coarse particle sifter (7) is further used as mash suitable for ethanol, bioethanol, starch, and syrup industries.

Example 1

Peeled wheat (with peeling depth of 6% of the wheat kernel mass) is milled using a grain mill, and mixed with water in a 1:2 ratio to form the batch. The batch is brought to 60 degrees C. and liquefaction enzymatic agents are added in the amount of one AC unit per one gram of starch. The mixture then undergoes mechano-activation in the rotary pulsing apparatus (RPA) 300 type apparatus in the range of oscillation frequencies between 1 and 200 kHz with impulse duration of 0.05 seconds and 20 processing cycles.

In alcohol production, substrate mechano-activation is used to activate enzymes either contained in the substrate being processed, or to activate enzymatic agents subsequently added to the mix. This process is facilitated by the dispersion of fine particles contained in the mixture (the colloidal mill effect). It has been found experimentally that the mechano-activation process is most efficient in the range of oscillation frequencies between 1 and 200 kHz, with impulse duration between 0.05 and 1.0 seconds for 2 to 20 processing cycles. The rotary pulsating apparatus (RPA) is a commonly used device in the mechanoactivation treatment.

It should be noted that existing equipment for mechano-activation process is quite demanding on (i.e. sensitive to) the mixture that is processed, namely in regard to abrasive and coarse particles present in the mixture. The presence of the latter may tend to clog up the equipment and may lead to equipment breakdown and/or leading to an increase in equipment maintenance. The present process can be made to reduce this problem, but still it must be realized that periodic maintenance is required.

The prototype of the present method is a method of mash preparation for ethanol production. The method provides milling the starch-containing material (wheat) using a grain mill, mixing the grain feed with water, acoustic oscillation treatment, thermal treatment, another acoustic oscillation treatment, cooking, cooling, saccharification and fermentation.

There are additional items (practical advices) that help to efficiently utilize the invention. These include: 1) The initial grain has to be thoroughly cleaned from impurities. 2) The initial grain dryness has to be controlled and maintained at a particular level (which depends on several factors such as equipment capabilities and characteristics, and end products desired). 3) The troublesome areas may include the grain peeler sieve separator, which needs periodical maintaining to prevent its clog up, and also periodical service of mechano-activation apparatus on the matter of rotor-stator clearance. 4) The temperature of the batch for mechano-activation preferably should have a temperature higher than ambient to improve process efficiency.

In regard to key ranges of the invention: 1) The peeling depth above depends on the particular cereal culture utilized. The point is that the total starch loss associated with the removal and separation of the outer layers of grain (i.e., "coat fractions") should preferably not exceed about 2% of the total starch content in the grain. In principle, outer grain layers, which do not contain any starch, may compose about 20% of the grain kernel mass. While it is possible to remove and separate the entire outer grain fraction, it is not reasonable as it can lead to a substantial loss (such as up to 8%) of the total starch content in the grain. The increase in the percentage removal of the outer grain layers is associated with a proportionately higher loss of the starch content. For example, the removal of 20% of the grain kernel mass is associated with a four-fold increase in the loss of starch compared with that of the 10% removal. The starch loss that takes place under the process described here is justified by the fact that the starch proximate to outer grain layers is most vulnerable to chemical modification during the crop drying process, making it not fermentable and, thus, not utilizable in further production process. Practice shows that this vulnerable starch fraction composes about 2% of the total grain starch content. 2) The oscillation frequencies above are noted as being between 1 and 200 kHz, with impulse duration between 0.05 and 1.0 sec for two to 20 processing cycles. However, in practice, it depends on equipment capabilities, and on how difficult it is to reach narrower and/or lower ranges of the oscillation frequencies. The number of processing cycles will depend on the efficiency of pre-stages and quality/sorting of material. In reference to FIG. 5, initially the post harvest cleaned grain stock is fed to the grain peeler (1) where the grain is subjected to mechanical surface treatment by friction or abrasion or a combination thereof, to remove flour bran and coarse bran with the peeling depth from 4% to 9% of the grain kernel mass. Simultaneously, flour bran is separated from the grain in the grain peeler (1) by particle size differences. Thereafter (in FIG. 5), the stock is passed through the aspiration separator (2) in order to separate coarse bran from the grain. The separation in the aspiration separator is achieved based on difference in particle velocity and size.

After the separation (continuing in FIG. 5), the grain stock is passed through a block valve (10) to the grain mill (3) for milling. Thereafter, the stock is passed to the air sieve separator (4) in order to separate husk bran in amount of 2%-3% of the grain kernel mass from endosperm flour by differences in particle size. Thereafter, endosperm flour is mixed with water in the mixing tank (5). Liquefying enzymatic agents are added to the batch, and the batch undergoes mechano-activation in the colloid mill (6) in the range of oscillation frequencies between 1 and 200 kHz, with impulse duration between 0.05 and 1.0 seconds. Then the batch is split into two flows: the first flow being recycled back to the mixing tank (5) and the second flow (often called "batch permeate") permeating through the coarse particle sifter (7). The quantity of the batch processing cycles in the circuit of: mixing tank (5), colloid mill (6), and coarse particle sifter (7) is between 2 and 20 times (i.e., processing "cycles"). The batch permeate flowing through the coarse particle sifter (7) is further used as mash suitable for ethanol, bioethanol, starch, and syrup industries. The outer layers (bran), which are removed during the separation stages, are collected as byproduct for further processing and use. As evident from the above description, the proposed method requires no water. It is noted that the grain peeler separation chamber may clog and require periodic cleaning of the chamber for stable operation.

It is to be understood that variations and modifications can be made on the aforementioned structure without departing from the concepts of the present invention, and further it is to be understood that such concepts are intended to be covered by the following claims unless these claims by their language expressly state otherwise.

The embodiments of the invention in which an exclusive property or privilege is claimed are defined as follows:

1. A process of dry cereal grain treatment for ethanol, bioethanol, starch and syrup industries comprising the steps of:
   providing post harvest cleaned grain stock;
   mechanically treating the surface of the unmilled grain to remove coarse bran and flour bran from remaining grain product;
   separating of the coarse bran and flour bran from the remaining grain product;
   milling the remaining grain product to form a milled grain product; and
   separating the husk bran from the milled grain product.

2. A process according to claim 1, wherein no water is added during the process.

3. A process according to claim 1, wherein the process does not include a step of tempering or conditioning the unmilled grain nor the remaining grain product.

4. A process according to claim 1, wherein the steps of separating impurities and mechanically treating the surface are combined into a single step.

5. A process according to claim 1, including separating outer layers of the milled grain product from the grain endosperm by separating flour bran based on particle size difference, separating coarse bran based on difference in particle velocity and size, and separating husk bran from endosperm flour based on particle size difference.

6. A process according to claim 1, wherein outer layers with the peeling depth from 4% to 9% of the grain kernel mass are removed and further separated.

* * * * *